US006391591B1

(12) United States Patent
Petersen et al.

(10) Patent No.: US 6,391,591 B1
(45) Date of Patent: May 21, 2002

(54) BIOTECHNOLOGICAL PROCESS FOR PREPARING N-ACETYLMANNOSAMINE

(75) Inventors: Michael Petersen, Visp; Klaus Heinzmann, Visperterminen, both of (CH)

(73) Assignee: Lonzo Ltd. (CH)

( * ) Notice: Subject to any disclaimer, the term of this patent is extended or adjusted under 35 U.S.C. 154(b) by 0 days.

(21) Appl. No.: 09/624,982

(22) Filed: Jul. 25, 2000

Related U.S. Application Data

(60) Provisional application No. 60/146,104, filed on Jul. 29, 1999.

(51) Int. Cl.⁷ .................................................. C12P 19/26
(52) U.S. Cl. .............................. 435/84; 435/41; 435/44; 435/105; 435/243
(58) Field of Search ............................. 435/84, 41, 44, 435/243, 105

(56) References Cited

PUBLICATIONS

Spivak, C.T., and S. Roseman, JACS, vol. 81, (May 20, 1959), pp. 2403 to 2404.

Kulla et al., Arch. Microbiol., (1983), pp. 1 to 7.

Kuhn, R. and G. Barschang, Liebigs Ann., 659, (1962), pp. 156 to 163.

Kuboki et al., vol. 53, No. 7, (1997), pp. 2387 to 2400.

*Chemical Abstracts*, vol. 130, No. 14 (Apr. 5, 1999), 179758.

*Primary Examiner*—Francisco Prats
*Assistant Examiner*—Kailash C. Srivastava
(74) *Attorney, Agent, or Firm*—Fisher Christen & Sabol

(57) ABSTRACT

Novel microorganisms, which can be obtained by the following selection method:

(a) microorganisms which grow using N-acetylglucosamine as the sole carbon source are cultivated in a customary manner, (b) from the resulting culture, these microorganisms are then selected which are stable and have the property to metabolize N-acetylglucosamine rapidly in the presence of N-Acetylmannosamine.

Furthermore, a novel process for preparing NAM starting from a mixture of NAM and NAG.

15 Claims, No Drawings

BIOTECHNOLOGICAL PROCESS FOR PREPARING N-ACETYLMANNOSAMINE

This application claims the benefit of and the priority of U.S. Provisional Application Serial No. 60/146,104, filed on Jul. 29, 1999, and is a continuing application of International application PCT/EP00/01892, with an international filing date of Mar. 3, 2000.

BACKGROUND OF THE INVENTION

1. Field of the Invention

The present invention relates to novel microorganisms and to a novel biotechnological process for preparing or enriching N-acetylmannosamine using these microorganisms.

2. Background Art

N-Acetylmannosamine (hereinbelow referred to as NAM) is an important intermediate in the preparation of N-acetylneuraminic acid (hereinbelow referred to as NANA), which in turn is an important starting material for therapeutic agents (European Published Patent Application No. 0701623).

To date, a plurality of biotechnological process for preparing or enriching NAM are known. Spivak C. T. & Roseman S. (JACS, Volume 81, 1959, pp. 2403 to 2404) describe the enrichment of NAM using washed microorganisms of the species *E. coli*, which have been adapted such that they can grow using N-acetylglucosamine (hereinbelow referred to as NAG) as the sole carbon source. This process has the disadvantages that it is not feasible industrially, and that NAM is obtained in only moderate yield.

Kuboki et al., (Tetrahedron, Vol. 53, 1997, pp. 2387 to 2400), describes a process for enriching NAM using washed microorganisms of the species *Rhodococcus rhodochrous*, where NAM is enriched starting from a mixture comprising NAM and NAG in a ratio of 4.5:1 (82:18). In this process, too, NAM is enriched in an uneconomical, not industrially feasible, manner.

BRIEF DESCRIPTION OF THE INVENTION

The object of the present invention is to provide a microorganism and a biotechnological process for preparing or enriching NAM, where the desired product is enriched rapidly in a simple manner. This object is achieved with microorganisms which are in accordance with the present invention obtainable by selecting microorganisms using N-Ac-Glc rapidly as sole carbon source for growth and are stable and can metabolize N-Ac-Glc rapidly in the presence of N-Ac-Man and with a process employing said microorganisms for preparing N-Ac-Man by the microorganism of the invention and the process of the invention.

The microorganisms according to the invention can be isolated from soil samples, mud or wastewater with the aid of customary microbiological techniques. According to the invention, the microorganisms are isolated in such a manner that they are cultivated in a customary manner in a medium comprising NAG as the sole carbon source, and with a suitable nitrogen source. From the culture obtained by cultivation, those are selected which are stable and have the property to metabolize NAG rapidly in the presence of NAM.

The invention includes biologically pure cultures of the microorganisms of the invention.

Advantageously, the microorganisms selected in such a manner metabolize NAG in a concentration of 60 g/l in less than 30 hours.

A suitable nitrogen source which can be used by the microorganisms is, for example, ammonium.

The selection medium used can be the mineral salt media customarily used by persons skilled in the art, such as, the medium described in Table 1, the mineral salt medium according to Kulla et al., Arch. Microbiol. (1983), 135, 1 to 7, or buffers of low molarity comprising mineral salts/trace elements. Preference is given to using the medium described in Table 1 of Kulla et al, ibid. The buffer of low molarity used can, for example, be a phosphate buffer of low molarity.

The selection is generally carried out at a temperature of from 15° to 60° C., advantageously from 25° to 45° C., and at a pH between pH 4 and pH 9, advantageously between pH 6 and pH 8.

Preferred microorganisms are microorganisms of the genus Klebsiella, advantageously of the species *Klebsiella pneumoniae* having the designation KHA (DSM 12702) and KHA1 (DSM 12703) or their "functionally equivalent variants". The microorganisms having the designation DSM 12702 and DSM 12703 were deposited with the Deutsche Sammiung von Mikroorganismen und Zellkultur GmbH, Mascheroderweg 1b, D-38124 Brunswick, in accordance with the Budapest Treaty, on Feb. 23, 1999.

DETAILED DESCRIPTION OF THE INVENTION

"Functionally equivalent variants" are to be understood as microorganisms which essentially have the same properties and functions as the original microorganisms. Such variants can be formed arbitrarily, for example, by UV irradiation or other mutagenesis techniques known to a person skilled in the art.

| Taxonomic description of *Klebsiella pneumoniae* with the name KHA (DSM 12702) | |
|---|---|
| Cell form | Rods |
| Width, μm | 0.8–1.0 |
| Length, μm | 1.2–2.5 |
| Motility | − |
| Gram reaction | − |
| Lysis by 3% KOH | + |
| Aminopeptidase (Cerny) | + |
| Oxidase | − |
| Formation of acid from: | |
| D-Glucose | + |
| D-Xylose | + |
| Erythritol | − |
| Adonitol | − |
| D-Mannose | + |
| Rhamnose | + |
| Inositol | + |
| Sucrose | + |
| α-Methyl-D-glucose | + |
| Inulin | − |
| Cellobiose | + |
| Maltose | + |
| Lactose | + |
| 5-Ketogluconate | + |
| L-Sorbose | + |
| Dulcitol | + |
| β-Galactosidase | + |
| ADH (alcohol dehydrogenase) | − |
| LDC (lactate decarboxylase) | − |
| ODC (ornithine decarboxylase) | − |
| Voges Proskauer | + |
| Indol | − |
| Malonate utilization | + |

-continued

Taxonomic description of Klebsiella pneumoniae
with the name KHA (DSM 12702)

| Cell form | Rods |
|---|---|
| H₂S formation | − |
| Citrate utilization (Simmons) | + |
| Phenylalanine desaminase | − |
| Urease (3 d) | |
| Hydrolysis of: | |
| Gelatin | − |
| DNA | − |
| Tween 80 | |

Taxonomic description of Klebsiella pneumoniae
with the name KHA 1 (DSM 12703)

| Cell form | Rods |
|---|---|
| Width μm | 0.8–1.0 |
| Length μm | 1.2–2.5 |
| Motility | − |
| Gram reaction | − |
| Lysis by 3% KOH | + |
| Aminopeptidase (Cerny) | + |
| Oxidase | − |
| Catalase | + |
| Formation of acid from: | |
| D-Glucose | + |
| D-Xylose | + |
| Erythritol | − |
| Adonitol | − |
| D-Mannose | + |
| Rhamnose | + |
| Inositol | + |
| Sucrose | + |
| α-Methyl-d-glucose | + |
| Inulin | + |
| Cellobiose | + |
| Maltose | + |
| Lactose | + |
| 5-Ketogluconate | + |
| L-Sorbose | + |
| Dulcitol | − |
| β-Galactosidase | + |
| ADH (alcohol dehydrogenase) | − |
| LDC (lactate decarboxylase) | w |
| ODC (ornithine decarboxylase) | − |
| Voges Proskauer | + |
| Indol | − |
| Malonate utilization | + |
| H₂S formation | − |
| Citrate utilization (Simmons) | + |
| Phenylalanine desaminase | − |
| Urease (3 d) | + |
| Hydrolysis of: | |
| Gelatin | − |
| DNA | − |
| Tween 80 | − |

The process of according to the invention for preparing or enriching NAM is carried out such that, starting from an NAG/NAM mixture, NAG is metabolized by fermentation using the microorganisms according to the invention, NAM being enriched.

Advantageously, NAG is employed as a mixture comprising NAG and NAM in a ratio by weight of 1:1. This mixing ratio is preferably, according to R. Kuhn & G. Barschang (Liebigs Ann., 659, 1962, pp. 156 to 163), obtained by epimerizing the NAG, which was hydrolyzed from chitin, in a basic medium, resulting in a thermodynamical equilibrium of NAG to NAM of 4:1 parts by weight. This mixture is then enriched in accordance with the literature reference described above by selective removal of NAG, for example, by crystallization, so that a mixing ratio of NAM:NAG of 1:1 results.

In principle, the further enrichment according to the invention of NAM is possible using any NAG-metabolizing microorganisms which can be obtained by the selection method already described. In particular, the enrichment is carried out using the microorganisms of the genus Klebsiella, more preferably of the species *Klebsiella pneumoniae*. In a most preferred embodiment, the invention is carried out using strains of *Klebsiella pneumoniae* having the designation KHA (DSM 12702) or KHA1 (DSM 12703) or their "functionally equivalent variants".

The enrichment of NAM is advantageously carried out directly by fermentation of the selected microorganisms on the NAG/NAM mixture (i.e., with growing cells under aerobic conditions), without removing and washing the microorganisms beforehand, for example, by centrifugation.

Suitable for use as fermentation media are the same media as those described above used for the selection, using the NAG/NAM mixture instead of NAG as the carbon source.

Advantageously, the metabolization of NAG is carried out such that the concentration is below 20 percent by weight, preferably below 10 percent by weight. In particular, the appropriate NAG/NAM mixture is added once, batch-wise (in a plurality of portions) or continuously. The pH of the medium can be in the range of from 5 to 9, preferably from 6 to 8. The metabolization is advantageously carried out at a temperature of from 20° to 50° C., preferably from 25 to 40° C.

After customary metabolization of less than 30 hours, the NAM enriched in this manner can be isolated by customary work-up methods, such as, by electrodialysis, filtration techniques and crystallization EXAMPLE 1
Enrichment of Microorganisms Which Grow Using NAG 100 ml of mineral salt medium (cf. Table 1 below) containing 2 g/l of NAG was inoculated with 2 g of moist clarifier sludge and incubated in a 500 ml Erlenmeyer flask fitted with flow spoilers at 30° C. on a shaker table. 5 ml of this suspension was used to inoculate a further flask containing 100 ml of mineral salt medium and 2 g/l of NAG, and cultivation was carried out at 30° C. on a shaker table. After 3 days, a further passage was carried out. Individual colonies were obtained by plating out a dilution series and streaking out for purification purposes on agar plates of the enrichment medium described above (cultivated at 30° C.). In this manner, inter alia, the two strains KHA (DSM 12702) and KHA1 (DSM 12703) were isolated.

EXAMPLE 2
Selection of Microorganisms Which Grow Using NAG but not NAM as Sole Carbon Source Microorganisms which grow using NAG as sole carbon source (for example from the enrichment according to Example 1) were spread out on agar plates containing mineral salt medium (cf. Table 1 below) and 5 g/l of NAG and mineral salt medium (cf. Table 1 below) and 5 g/l of NAM, respectively, and cultivated at 30° C. The microorganisms which grew rapidly on NAG plates but only very slowly, if at all, on NAM plates were selected. In this manner, inter alia, the two strains KHA (DSM 12702) and KHA1 (DSM 12703) were selected.

EXAMPLE 3

Selection for Rapid Growth in the Presence of Elevated NAG Concentrations 100 ml of mineral salt medium (cf. Table 1 below) containing 5 g/l, 10 g/l, 20 g/l and 40 g/l of NAG was inoculated from the agar plate (containing NAG in accordance with Ex. 2) and cultivated in a 500 ml Erlenmeyer flask fitted with flow spoilers at 30° C. on a shaker table. By monitoring the optical density, it was possible to examine the growth rate under the different conditions. Strains which grew very rapidly and in the presence of elevated NAG concentrations were selected.

| Strain KHA | OD (650) after 18 h | OD (650) after 42 h |
|---|---|---|
| 5 g/l NAG | 4.2 | 4.5 |
| 10 g/l NAG | 6.5 | 8.5 |
| 20 g/l NAG | 8.2 | 13.8 |
| 40 g/l NAG | 9.1 | 14.7 |

EXAMPLE 4

Preparation of an NAG/NAM Mixture in the Ratio 1:1

1kg of NAG was dissolved in 3 l of water, the pH was adjusted to >11 using 30 percent strength aqueous sodium hydroxide solution and the mixture was allowed to stand at 20° to 40° C. for 1 to 2 days until an NAG/NAM ratio of about 4:1 had been reached. The solution was neutralized using sulfuric acid and concentrated under reduced pressure to about 30 percent. 0.6 kg of NAG crystallized out and was filtered off and was able to be recycled into the same reaction. The filtrate (0.8–1 l) contained 0.4 kg of NAG/NAM in a ratio of 1:1 (according to GC analysis).

EXAMPLE 5

Selection for Rapid Growth in the Presence of Elevated NAM Concentrations or Simple Batch Process 2 l of the mineral salt medium (cf. Table 1 below) containing 40 g/l of an NAG/NAM mixture (1:1) was inoculated with 80 ml of a preculture of the strain KHA or KHA1 (grown overnight on mineral medium containing 5 g/l of NAG; OD>4) and fermented at pH 7, 30° C., with aeration and stirring. After 16 hours, the OD (650 nm) was 13.7 (strain KHA) and 15.5 (strain KHA1), respectively, and only traces of NAG, if any at all, were found in the medium, which did however contain NAM (GC analysis; NAG:NAM <5:95). Strains such as *Klebsiella pneumoniae* KHA (DSM 12702) and KHA1 (DSM 12703), which grew rapidly and selectively on NAG in the presence of NAM were selected.

EXAMPLE 6

Fed Batch Process 1.5 l of mineral salt medium (cf. Table 1 below) containing 40 g/l of an NAG/NAM mixture (1:1) was inoculated with 100 ml of a preculture of the strain KHA (grown overnight on mineral medium containing 10 g/l of NAH; OD>4) and fermented at pH 7, 30° C., with aeration (1.5 l of air/min) and stirring (500 rpm). After 14 hours, 360 ml of a 46 percent strength solution of NAG/NAM mixture (1:1) (total: 113 g of NAG, 113 g of NAM; corresponding in each case to 57 g/l) was added. After 29.5 hours, the OD (650 nm) was 38.5, and only traces of NAG, if any at all, were found in the medium, which did however contain NAM (GC analysis; NAG;NAM <5:95).

EXAMPLE 7

Fed Batch Process, NAG/NAM Mixture (2:1)

1.5 l of mineral salt medium (cf. Table 1 below) containing 40 g/l of an NAG/NAM mixture (2:1) were inoculated with 100 ml of a preculture of the strain KHA1 (grown overnight on mineral medium containing 10 g/l of NAG; OD 0.4) and fermented at pH 7, 30° C., with aeration (1.5 l of air/min) and stirring (500 rpm). After 16 hours, 240 ml of a 46 percent strength solution of an NAG/NAM mixture (2:1) was added (total: 114 g of NAG=60 g/l, 57 g of NAM=30 g/l). After 22.5 hours, the OD (650 nm) was 43.4, and only traces of NAG, if any at all, were found in the medium, which did however contain NAM (GC analysis; NAG:NAM<5:95).

TABLE 1

Mineral salt medium (pH 7.0)

2.0 g/l $(NH_4)_2SO_4$,
2.0 g/l $Na_2HPO_4$,
1.0 g/l $KH_2PO_4$,
2.0 g/l NaCl,
0.4 g/l $MgCl_2 \times 6H_2O$,
14.5 mg/l $CaCl_2 \times 2H_2O$,
0.8 mg/l $FeCl_3 \times 6H_2O$,
0.1 mg/l $ZnSO_4 \times 7H_2O$,
0.09 mg/l $MnCl_2 \times 4H_2O$,
0.3 mg/l $H_3BO_4$,
0.2 mg/l $CoCl_2 \times 6H_2O$,
0.01 mg/l $CuCl_2 \times 2H_2O$,
0.02 mg/l $NiCl_2 \times 6H_2O$,
0.03 mg/l $NaMoO_4 \times 2H_2O$,
5.0 mg/l $EDTA \times 2Na \times 2H_2O$,
2.0 mg/l $FeSO_4 \times 7H_2O$.

What is claimed is:

1. A biotechnological process for preparing N-acetylmannosamine with microorganisms of the Genus Klebsiella, comprising the step of fermentatively metabolizing N-acetylglucosamine as a source of carbon from a mixture with N-acetylmannosamine, thereby enriching the N-acetylmannosmine, wherein the microorganisms of the Genus Klebsiella were prepared by culturing with N-acetylglucosamine as the sole carbon source, and thereby selecting the microorganisms which metabolized N-acetylglucosamine more rapidly than N-acetylmannosamine.

2. The process according to claim 1, wherein the microorganisms are, after selection and cultivation, employed directly for the fermentative metabolism of N-acetylglucosamine.

3. A biotechnological process for preparing N-acetylmannosamine with microorganisms of the Genus Klebsiella, comprising the step of fermentatively metabolizing N-acetylglucosamine as a source of carbon from a mixture with N-acetylmannosamine, thereby enriching the N-acetylmannosmine, wherein the microorganisms of the Genus Klebsiella were prepared by culturing with N-acetylglucosamine as the sole carbon source, and thereby selecting the microorganisms which had the property to metabolize N-acetylglucosamine in a concentration of 60 g/l in less than 30 hours more rapidly than N-acetylmannosamine.

4. The process according to claim 3, wherein the microorganisms are, after selection and cultivation, employed directly for the fermentative metabolism of N-acetylalucosamine.

5. A biotechnological process for preparing N-acetylmannosamine according to claim 1 or 3, wherein the microorganisms are *Klebsiella pneumoniae*.

6. The process according to claim 3, wherein the fermentative metabolism is carried out by cultivating *Klebsiella pneumoniae* strains KHA (DSM 12702) or KHA 1 (DSM 12703) or a variant thereof capable of metabolizing N-acetylglucosamine more rapidly than N-acetylmannosamine.

7. The process according to claim 1, wherein the fermentative metabolism is carried out by cultivating *Klebsiella pneumoniae* strains KHA (DSM 12702) or KHA 1 (DSM 12703) or a variant thereof capable of metabolizing N-acetylglucosamine more rapidly than N-acetylmannosamine.

8. The process according to claim 3, wherein the fermentative metabolism is carried out at a temperature of from 20° C. to 50° C. and a pH of from 5 to 9.

9. The process according to claim 3, wherein the fermentative metabolism is carried out by cultivating *Klebsiella pneumoniae* strains KHA (DSM 12702) or KHA 1 (DSM 12703) or a variant thereof capable of metabolizing N-acetylglucosamine more rapidly than N-acetylmannosamine.

10. A biotechnological process for preparing N-acetylmannosamine, comprising the step of fermentatively metabolizing N-acetylglucosamine as a source of carbon from a mixture with N-acetylmcnnosamine, thereby enriching the N-acetylmannosmine using *Klebsiella pneumoniae* strains KHA (DSM 12702) and KHA1 (DSM12703) and variants thereof capable of metabolizing N-acetylglucosamine more rapidly than N-acetylmannosamine.

11. The process according to claim 10, wherein the microorganisms are employed directly for the fermentative metabolism.

12. The process according to claim 1, wherein the fermentative metabolism is carried out at a temperature of from 20° C. to 50° C. and a pH of from 5 to 9.

13. The process according to claim 2, wherein the fermentative metabolism is carried out by cultivating *Klebsiella pneumoniae* strains KHA (DSM 12702) or KHA 1 (DSM 12703) or a variant thereof capable of metabolizina N-acetylalucosamine more rapidly than N-acetylmannosamine.

14. The process according to claim 13, wherein the fermentative metabolism is carried out at a temperature of from 20° C. to 50° C. and a pH of from 5 to 9.

15. The process according to claim 9, wherein the fermentative metabolism is carried out at a temperature of from 20° C. to 50° C. and a pH of from 5 to 9.

* * * * *